United States Patent
Fischer et al.

(10) Patent No.: US 10,893,909 B2
(45) Date of Patent: Jan. 19, 2021

(54) CONTROL METHOD FOR A ROBOTIC DEVICE WITH AN ULTRASOUND APPARATUS AND ROBOTIC DEVICE

(71) Applicant: Siemens Healthcare GmbH, Erlangen (DE)

(72) Inventors: Peter Fischer, Erlangen (DE); Philip Mewes, Nuremberg (DE); Holger Mönnich, Friedberg (DE); Gunter Müller, Heroldsberg (DE)

(73) Assignee: Siemens Healthcare GmbH, Erlangen (DE)

( * ) Notice: Subject to any disclaimer, the term of this patent is extended or adjusted under 35 U.S.C. 154(b) by 237 days.

(21) Appl. No.: 16/145,520

(22) Filed: Sep. 28, 2018

(65) Prior Publication Data
US 2019/0099223 A1    Apr. 4, 2019

(30) Foreign Application Priority Data
Sep. 29, 2017   (EP) ..................................... 17194033

(51) Int. Cl.
*A61F 5/00* (2006.01)
*A61B 34/20* (2016.01)
(Continued)

(52) U.S. Cl.
CPC .......... *A61B 34/20* (2016.02); *A61B 17/1703* (2013.01); *A61B 34/30* (2016.02);
(Continued)

(58) Field of Classification Search
CPC combination set(s) only.
See application file for complete search history.

(56) References Cited

U.S. PATENT DOCUMENTS

| 2017/0151025 | A1 | 6/2017 | Mewes et al. |
| 2019/0231458 | A1* | 8/2019 | DiMaio .................. A61B 34/70 |

FOREIGN PATENT DOCUMENTS

WO    0033723 A2    6/2000

OTHER PUBLICATIONS

European Office Action for European Patent Application No. 17194033.1-1115 dated Mar. 27, 2018.
(Continued)

*Primary Examiner* — Sameh R Boles
(74) *Attorney, Agent, or Firm* — Lempia Summerfield Katz LLC

(57) ABSTRACT

A method is provided for controlling a robotic device, of which the end effector arranged on a kinematic chain interacts with an object, and including an ultrasound apparatus registered to the robotic device for movement capture of the object. Ultrasound image data of the object is captured. The relative movement of the object is determined on the basis of the ultrasound image data using a mathematical method. The absolute movement is determined through registration to a planning data set. Movements of the object are compensated for in the context of the interaction of the end effector of the robotic device with the object. Future movements of the object and a positioning of the end effector of the robotic device adapted thereto are predicted and the robotic device is controlled accordingly. In the calculation of the adapted positioning of the end effector of the robotic device, a temporal delay relative to the movement of the object is included.

12 Claims, 3 Drawing Sheets

(51) Int. Cl.
*A61B 34/30* (2016.01)
*A61B 17/17* (2006.01)
*B25J 9/16* (2006.01)
*B25J 11/00* (2006.01)
*A61B 90/00* (2016.01)

(52) U.S. Cl.
CPC ......... *B25J 9/1697* (2013.01); *B25J 11/0055* (2013.01); *A61B 2034/2063* (2016.02); *A61B 2090/378* (2016.02)

(56) References Cited

OTHER PUBLICATIONS

Ginhoux, Romuald, et al. "Active filtering of physiological motion in robotized surgery using predictive control." IEEE Transactions on Robotics 21.1 (2005): 67-79.

Reichl, Tobias, José Gardiazabal, and Nassir Navab. "Electromagnetic servoing—a new tracking paradigm." IEEE transactions on medical imaging 32.8 (2013): 1526-1535.

Yuen, Shelten G., et al. "3D ultrasound-guided motion compensation system for beating heart mitral valve repair." International Conference on Medical Image Computing and Computer-Assisted Intervention. Springer, Berlin, Heidelberg, 2008.

* cited by examiner

CONTROL METHOD FOR A ROBOTIC DEVICE WITH AN ULTRASOUND APPARATUS AND ROBOTIC DEVICE

CROSS REFERENCE TO RELATED APPLICATIONS

This patent application claims priority from European Patent Application no. 17194033.1 filed on Sep. 29, 2017, which is hereby incorporated in its entirety.

FIELD

Embodiments relate to a control method for a robotic device with an ultrasound apparatus.

BACKGROUND

The greatest possible precision is used in the field of robotic surgical interventions that may be both diagnostic as well as therapeutic and in which an object is controlled by a robotic device or an interaction is carried out with the object. An example is found in robot-assisted spinal surgery in which a drilling sleeve is held by a robotic device, by which a screw or another instrument is introduced into a bone of the patient.

Current robotic systems and methods in the field often function with external optical tracking systems that include, for example, a camera and a marker to be able to record movements of the object (e.g. breathing movement or heart movement in a patient) precisely. The markers are physically fastened to the object and then directly followed with the camera, so that a direct sight connection is required. The movements of the object may be optically tracked. The application of the marker to the object and the requirement of an unobstructed line of sight for the camera, however, are often limiting and undesirable. Other systems for tracking patient movements, such as EMT tracking or live fluoroscopy have disadvantages, hinder the workflow, are invasive or entail risks through unnecessary X-ray radiation.

In the European patent application with the application number 17159352.8, a system and a method are known in which for movement capture, a 3-D ultrasound apparatus is arranged, for example, directly on a robotic device that captures the movements of the object in all three dimensions. In addition to the movement capture, however, a control of the robotic device is also necessary in order to be able to compensate for detected movements exactly with the robotic device and without risk to the patient.

SUMMARY AND DESCRIPTION

The scope of the present disclosure is defined solely by the appended claims and is not affected to any degree by the statements within this summary. The present embodiments may obviate one or more of the drawbacks or limitations in the related art.

Embodiments provide a method for control of a robotic device with an ultrasound apparatus, by which a precise detection and compensation of movements of an object is possible.

In an embodiment, a method is provided for controlling a robotic device, of which the end effector arranged on a kinematic chain interacts with an object, and including an ultrasound apparatus registered to the robotic device for movement capture of the object, including: capturing of ultrasound image data of the object, determining of the relative movement of the object on the basis of the ultrasound image data using a mathematical method, determining of the absolute movement through registration to a planning data set, and compensating of movements of the object in the context of the interaction of the end effector of the robotic device with the object. On the basis of the current movement determination, future movements of the object and a positioning of the end effector of the robotic device adapted thereto are predicted, and the robotic device is controlled. In the calculation of the adapted positioning of the end effector of the robotic device, a temporal delay relative to the movement of the object is included. The method provides a precise compensation of live movements of the object such that dangers, for example, from injury to the object or patient may be minimized. The background is the recognition that different processes, for example, the movement capture itself, but also the response of the robotic device to a control signal require a particular time for their execution. In order to carry out the compensation as precisely as possible, future movements of the object and planned movements of the robotic device are calculated taking account of the temporal delay. In place of "tracking" the movement of the robotic device with a temporal delay, as is known from the prior art, the future movement of the object is predicted and "adjusted" by the robotic device.

The movements of the object may be periodic, e.g. globally the breathing or heartbeat of the object (patient) or locally a movement that accelerates or decelerates.

In an embodiment, in the determination or estimation of the temporal delay, at least the duration of the acquisition of the ultrasound image data, the duration of the determination of the absolute movement and the reaction time of the robotic device are taken into account that each contribute to the temporal delay. Further factors may also be taken into account in order to determine the actual delay, for example, the duration of the pre-calculations of the positions of the object and the robotic device.

In an embodiment, in the context of the mathematical method for determining the relative movement of the object, features are extracted from image data. The features may be transformed, for example, spatially onto features of further images. For example, the mathematical method for determining the relative movement of the object may use the image processing methods feature extraction or optical flow. Other image processing methods may also be used.

For the execution of an intervention extending over a relatively long time period, a continuous movement capture and movement compensation may be carried out up to a stop criterion.

For a rapid movement calculation, the ultrasound apparatus may be registered to a patient coordinate system.

In an embodiment, the predicted positions of the end effector of the robotic device are filtered and/or synchronized. The two methods provide for preventing measurement noise and measurement errors as well as sudden movements and movements of the object deviating from the normal movement flow, such as twitches, with the robotic device or where possible not to follow such movements. As an example, for a suitable known filter, the Kalman filter is used.

In order to compensate for the temporal delay, the robotic device accelerates significantly faster in order to synchronize with the movement of the object as performed by the object, while at the same time, the robotic device brakes at the right time in order not to overshoot the target.

For the method, a robotic device is used with an ultrasound apparatus registered to the robotic device. The robotic device includes a kinematic chain of movable components, an end effector arranged at the end of the kinematic chain. The end effector is configured for interaction with an object, a control device for controlling the kinematic chain and the ultrasound device, an image processing device and a computer unit. The ultrasound device is configured to capture ultrasound image data of the object. The image processing device and the computer unit are configured to be cooperative in order, from the ultrasound image data and the other data, to determine the relative movement and the absolute movement of the object, on the basis of the current movement determination, to calculate future movements of the object and to predict a positioning of the robotic device adapted thereto, with a temporal delay relative to the movement of the object included, and the control device is configured to control the positioning of the robotic device.

In an embodiment, the robotic device includes an end effector in the form of a drilling sleeve. The end effector may be used in connection with interventions for introducing or drilling screws or other implants into bone structures.

DETAILED DESCRIPTION

Figure 1:
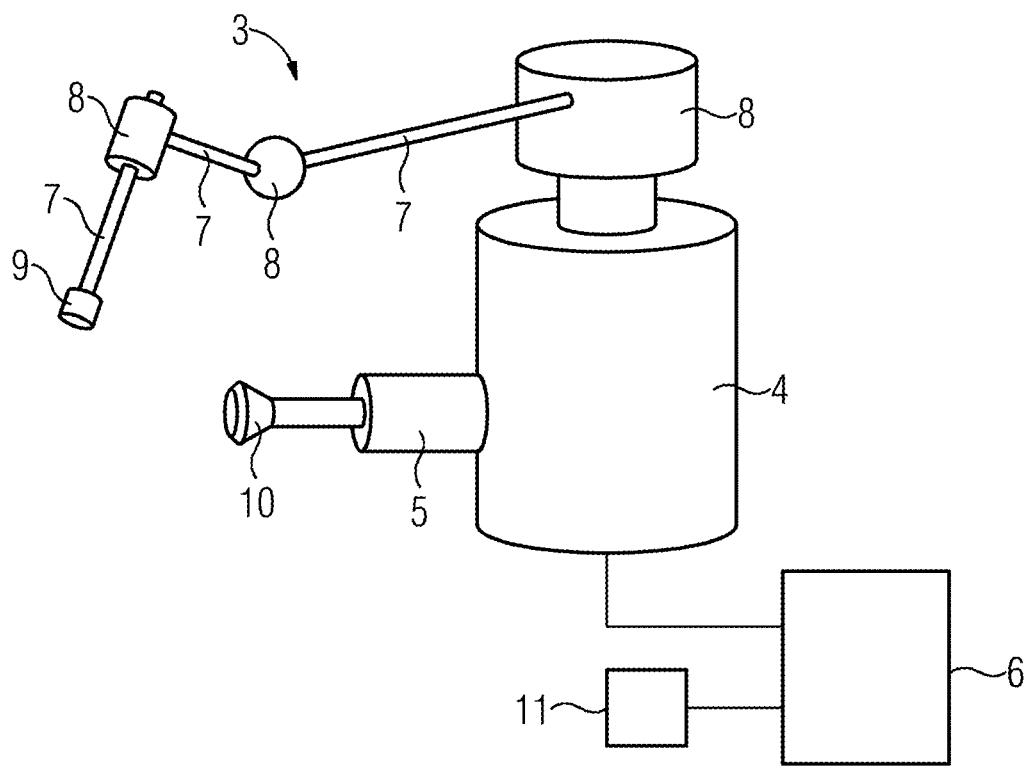
FIG. 1 depicts a robotic device with an ultrasound apparatus.

FIG. 1 depicts a robotic device 4 with an ultrasound apparatus 5 for movement capture, as described, for example, in the European patent application with the application number 17159352.8. The robotic device 4 includes a robot arm 3 that includes a plurality of (at least 3) segments 7 and joints 8 and on the free end an end effector 9. The end effector 9 is configured for interaction with an object, for example, a patient. An example of the use of such a robotic device is in robot-assisted spinal surgery. The end effector is configured, for example, as a drilling sleeve that is held by the robot arm. The drilling sleeve is placed on the bone of a patient and a screw or another instrument is introduced through the drilling sleeve by a surgeon. The ultrasound apparatus 5 is arranged, for example, on the robotic device 4 or is otherwise mechanically connected thereto and includes an ultrasound head 10 that is configured for recording (3-D) ultrasound image data. The ultrasound head 10 is brought into contact with the object. For controlling the robotic device 4 and the ultrasound apparatus, a control device 6 is provided and an image processing device 11 for processing the ultrasound image data may be used. In the case of a drilling sleeve, the ultrasound head may also, for example, be integrated.

Figure 2:
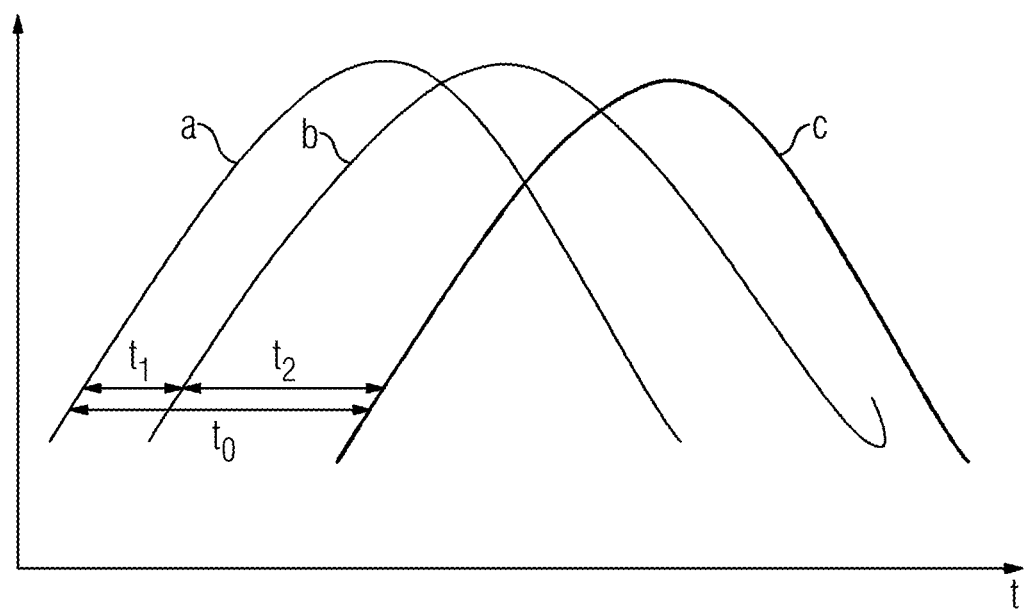
FIG. 2 depicts a temporal sequence of the movement of the object and a robotic device.

In FIG. 2, a time axis t is depicted to show how a movement delay comes about. A cyclic movement a of the object (e.g. breathing movement or heart movement of a patient) takes place. After a first time period $t_1$, the ultrasound image data is acquired and evaluated b and only after a second time period $t_2$ (e.g. reaction time of a robotic device), the movement c of the robotic device takes place. Overall, there results a temporal delay to between the movement a of the object and the movement of the robotic device c, so that a movement compensation based thereon is not of high quality. In the surgical field, a hazard to patients through, for example, injuries arise from the poor quality, so that a high quality movement compensation is needed instead.

Figure 4:
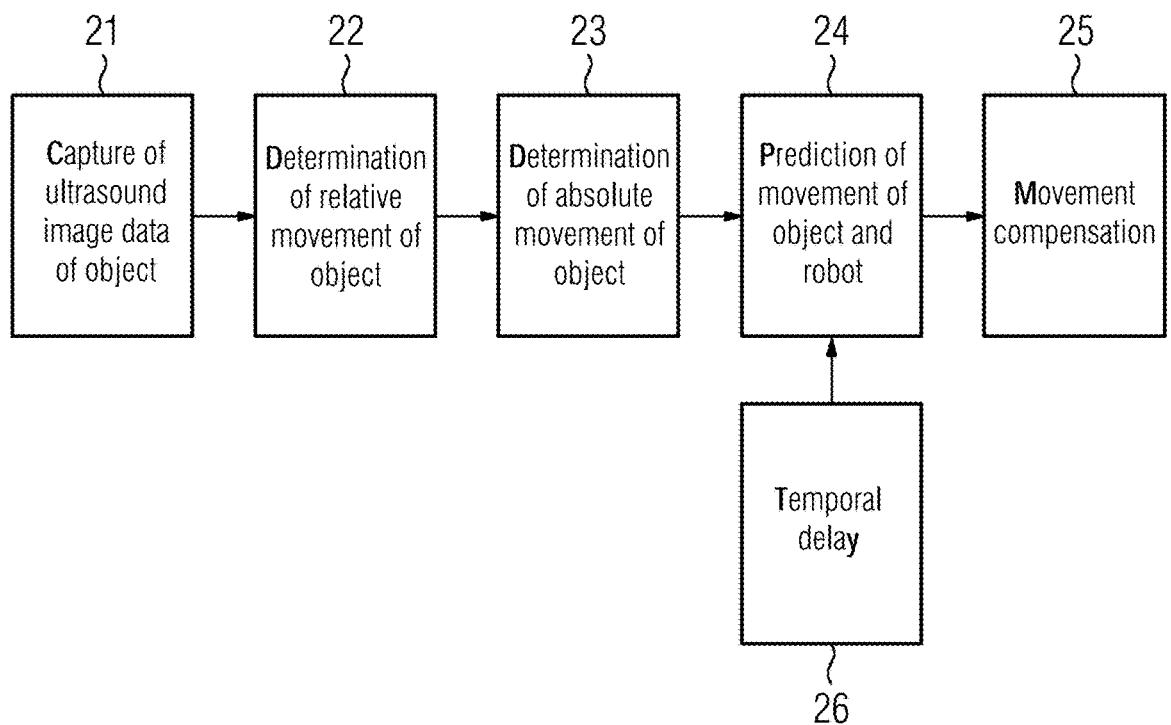
FIG. 4 depicts a sequence according to an embodiment.

FIG. 4 depicts a sequence of the method for controlling a robotic device that interacts with an object, and including an ultrasound apparatus registered to the robotic device for movement capture of the object. The method provides a precise and high quality movement compensation and may also be used in the surgical environment. Based upon the recognition that different processes, for example, the movement capture or the response of the robotic device to a control signal require a time for execution, the correspondingly necessary time is included as a temporal delay in the planned movement of the robotic device and adjusted with future predicted movements of the object.

The ultrasound apparatus is registered to an object coordinate system (e.g. a patient coordinate system). A movement of the robotic device may be a movement of the robot arm for positioning the end effector.

In a first act 21, using the ultrasound apparatus 5, ultrasound image data of a moving object (e.g. a patient) is recorded. Herein, the ultrasound head is in contact with the object involving at least two or a plurality of ultrasound images that may be 2-D or 3-D ultrasound image data. The movement of the object may be, for example, the cyclic breathing movement or the heart movement of a patient.

In a second act 22, the relative movement of the object is determined or calculated on the basis of the recorded ultrasound image data using a mathematical method. For example, for determining the relative movement of the object from the ultrasound image data, features of the object are extracted. Examples of methods may be feature extraction or so-called optical flow. There are many other possibilities for extracting a movement detection from the ultrasound image data.

In a third act 23, the absolute movement is determined by registration to a planning data set. The absolute movement is understood to be the temporally classified movement. A planning data set is understood to be a pre-existing initial data set, for example a 2-D or 3-D data set. The planning data set may be an ultrasound data set, although other data sets may also be used, for example X-ray image data. Vectors or image points generated from the second step 22 may be obtained, suitably filtered and, in the third act, registered to a previous image data set or to an existing initial 3-D or 2-D image data set. The result of the calculations may be, for example, a new position in the space or a speed vector that reflects the movement of the object (patient) to a defined point in the volume of the object (patient).

In a fourth act 24, a temporal delay in the planned movement of the robotic device is included and is synchronized with predicted future movements of the object. The necessary temporal delay may have been estimated, calculated or empirically determined, for example, in advance in an additional act 26 but, for example, a constant value may be used. Taken into consideration in the temporal delay are the recording of the ultrasound image data, the determinations of the movement of the object and the control of the robotic device in a duration. In addition, the duration for the prediction of the object movement and the planned movement of the robotic device may be included. In addition, dynamic limitations on the movement of the robotic device may be taken into account in the planning of the movement compensation. Thus, in some cases (e.g. twitches) the robotic device may not accelerate as fast as the patient or a movement must be synchronized, e.g. in the case of breathing or heartbeat, to avoid jerking. In order not also to predict movements that may not be followed (jerking) or measurement noise, the planned movements of the robotic device are generally filtered (e.g. with the so-called Kalman filter) in order to reduce measuring errors.

In order to compensate for the temporal delay, a position is predicted for the robotic device. The position is based upon the determination of the movement of the object from the movement capture. A periodic movement is used, e.g. globally the breathing or heartbeat of the object (patient) or locally a movement that accelerates or decelerates.

In a fifth act 25, the movement of the object is compensated by the robotic device. It can herein be necessary that the robotic device accelerates significantly more than in the movement of the object to be compensated for in order to be synchronous, and also brakes more severely in order not to travel beyond the planned target.

Figure 3:
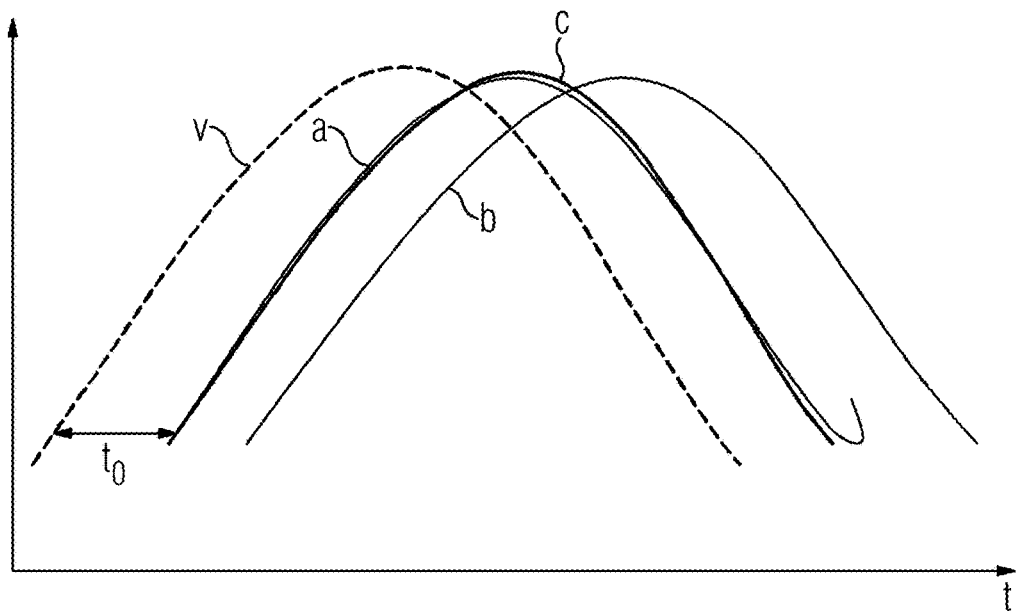
FIG. 3 depicts a temporal sequence making use of the movement compensation according to an embodiment with synchronization through prediction of the movement.

FIG. 3 depicts how the movements appear along the time axis t. The movement c of the robotic device is now synchronous, within the scope of an error tolerance, with the movement of the object a and the prediction V for the robotic device takes account of the temporal delay $t_0$.

Figure 5:
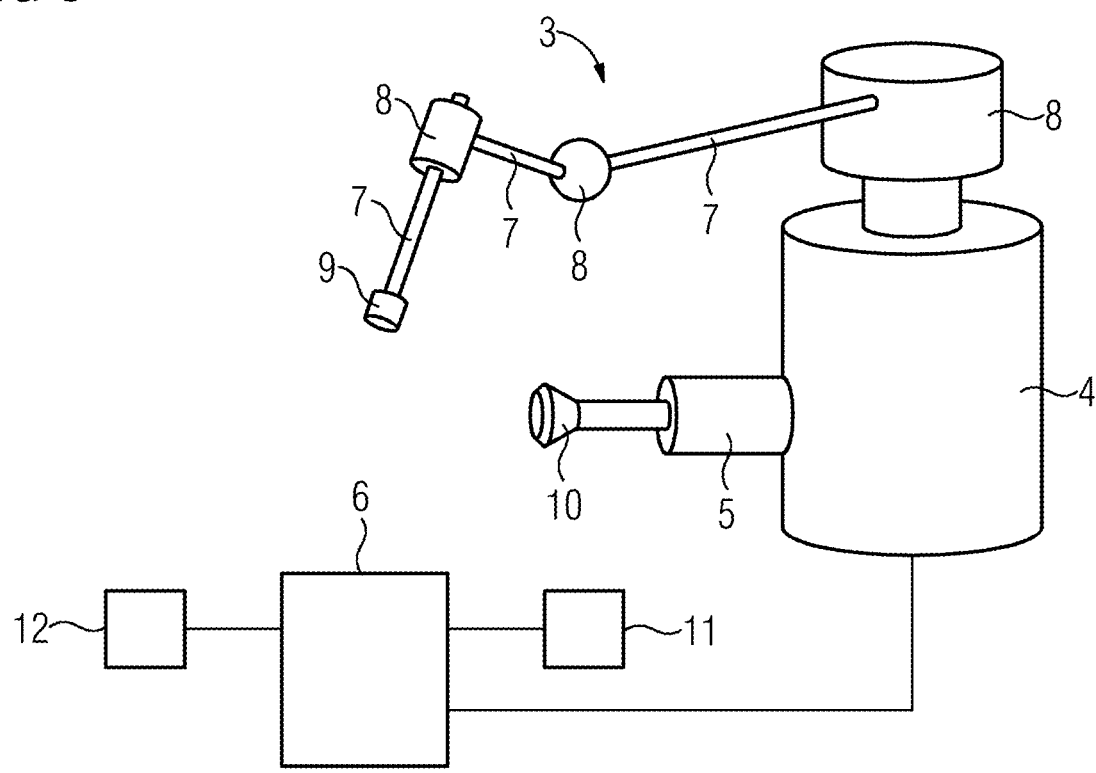
FIG. 5 depicts a robotic device according to an embodiment.

FIG. 5 depicts a robotic device 4 with an ultrasound apparatus 5 registered to the robotic device. The robotic device 4 includes a robot arm 3 that includes a plurality of (at least 3) segments 7 and joints 8 and on the free end, an end effector 9, for example, a drilling sleeve. The end effector 9 is configured for interaction with an object, for example, a patient or an organ of the patient. The robotic device includes a control device 6 for control of the robot arm and of the ultrasound apparatus 5. Furthermore, the robotic device includes an image processing device 11 and a computer unit 12. The ultrasound device is configured to capture ultrasound image data of the object. The image processing device 11 and the computer unit 12 are configured to be cooperative in order, from the ultrasound image data and other data (previously recorded image data or e.g. planning data), to determine the relative movement and the absolute movement of the object, on the basis of the current movement determination, to calculate future movements of the object and to predict a positioning of the robotic device adapted thereto, with a temporal delay relative to the movement of the object included. The control device 6 is configured to control the positioning of the end effector of the robotic device.

In an embodiment, for a safe medical intervention for an object (e.g. patient) with a robotic device, a method is provided for controlling a robotic device, of which the end effector arranged on a kinematic chain interacts with an object, and including an ultrasound apparatus registered to the robotic device for movement capture of the object, including the following steps: Capture of ultrasound image data of the object, determination of the relative movement of the object on the basis of the ultrasound image data using a mathematical method, determination of the absolute movement through registration to a planning data set, and compensation of movements of the object in the context of the interaction of the end effector of the robotic device with the object. On the basis of the current movement determination, future movements of the object and a positioning of the end effector of the robotic device adapted thereto are predicted, and the robotic device is controlled. In the calculation of the adapted positioning of the end effector of the robotic device, a temporal delay relative to the movement of the object is included.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for controlling a robotic device with an end effector arranged on a kinematic chain that interacts with an object, and including an ultrasound apparatus registered to the robotic device for movement capture of the object, the method comprising:
   capturing ultrasound image data of the object,
   determining a relative movement of the object based on the captured ultrasound image data using a mathematical method,
   registering the captured ultrasound data to a planning data set;
   determining an absolute movement of the object from the registration;
   compensating for movements of the object in a context of an interaction of the end effector of the robotic device with the object;
   predicting future movements of the object and a positioning of the end effector of the robotic device based on the determined relative movement and determined absolute movement; wherein in predicting the positioning of the end effector of the robotic device, a temporal delay relative to the movement of the object is included; and
   controlling the robotic device based on the predicted future movements of the object and the positioning of the end effector.

2. The method of claim 1, wherein the temporal delay takes into account at least the duration of the acquisition of the ultrasound image data, the determination of the absolute movement and the reaction time of the robotic device.

3. The method of claim 2, wherein in the mathematical method for determining the relative movement of the object, features of the object are extracted.

4. The method of claim 2, wherein up to a stop criterion, continuous movement capture and movement compensation is carried out.

5. The method of claim 2, wherein the ultrasound apparatus is further registered to a patient coordinate system.

6. The method of claim 2, wherein the predicted positions of the kinematic chain of the robotic device are filtered.

7. The method of claim 2, wherein the predicted positions of the end effector of the robotic device are synchronized.

8. The method of claim 1, wherein in the mathematical method for determining the relative movement of the object, features of the object are extracted.

9. The method of claim 1, wherein up to a stop criterion, continuous movement capture and movement compensation is carried out.

10. The method of claim 1, wherein the ultrasound apparatus is further registered to a patient coordinate system.

11. The method of claim 1, wherein the predicted positions of the kinematic chain of the robotic device are filtered.

12. The method of claim 1, wherein the predicted positions of the end effector of the robotic device are synchronized.

* * * * *